(12) United States Patent
Johanson (10) Patent No.: US 7,451,666 B2
(45) Date of Patent: Nov. 18, 2008

(54) APPARATUS AND TEST PROCEDURE FOR MEASURING THE COHESIVE, ADHESIVE, AND FRICTIONAL PROPERTIES OF BULK GRANULAR SOLIDS

(75) Inventor: Jerry R. Johanson, San Luis Obispo, CA (US)

(73) Assignee: JR Johanson, Inc., San Luis Obispo, CA (US)

( * ) Notice: Subject to any disclaimer, the term of this patent is extended or adjusted under 35 U.S.C. 154(b) by 317 days.

(21) Appl. No.: 11/332,077

(22) Filed: Jan. 13, 2006

(65) Prior Publication Data

US 2007/0163328 A1 Jul. 19, 2007

(51) Int. Cl.
*G01D 7/02* (2006.01)
(52) U.S. Cl. ...................................................... 73/866
(58) Field of Classification Search .................. None
See application file for complete search history.

(56) References Cited

U.S. PATENT DOCUMENTS

| 4,633,712 | A | * | 1/1987 | Scieszka | 73/866 |
|---|---|---|---|---|---|
| 4,854,175 | A | * | 8/1989 | Budhu | 73/841 |
| 5,289,728 | A | | 3/1994 | Johanson | |
| 6,003,382 | A | * | 12/1999 | Puri et al. | 73/841 |
| 2006/0046307 | A1 | * | 3/2006 | Brower et al. | 436/172 |

OTHER PUBLICATIONS

Jenike et al., Flow Properties of Bulk Solids, American Society for Testing Materials, vol. 60, 1960, pp. 1168-1190.

Jenike, Gravity Flow of Bulk Solids: Part 5 Testing the Flow Properties of Bulk Solids, vol. 52 Bulletin No. 108, Utah Engineering Experiment Station, Oct. 1961, pp. 182-207.

Peschl, Equipment for Measurement of Mechanical Properties of Bulk Materials, Powder Handling and Processing vol. 1, 1989, pp. 73-81.

Kolymbas and Wu, Recent Results of Triaxial Tests with Granular Materials, Powder Technology, vol. 60, 1990, pp. 99-119.

* cited by examiner

*Primary Examiner*—Robert R Raevis
(74) *Attorney, Agent, or Firm*—Thomas F. Lebens; Sinsheimer Juhnke Lebens & McIvor, LLP (57) ABSTRACT

A test apparatus for measuring the cohesive, adhesive and frictional properties of bulk solids has a bulk solid sample confined between two essentially parallel plates with a single load applied that produces both shear and normal stress and strain to the bulk solid in a manner that nearly uniformly distributes stress throughout the granular solid test region. The apparatus has a close proximity of the plates compared with the length of the plates in the direction of shear, the design of a load hanger to produce a resultant load near the shear plane, the roughening of any surface in contact with the solid that is not intended to have shear on it and involves one-directional movement of the parallel plates with respect to each other and the control of both the direction and magnitude of the applied load relative to the parallel plates. A test method uses the apparatus to measure the unconfined yield strength angle of internal friction and steady state deformation effective angle of internal friction with a single test. A test method uses replacement of the lower part of the test sample with a plate of material that the bulk solid may be required to slip on and measures the friction angle and adhesion of the bulk solid on the plate of material.

12 Claims, 8 Drawing Sheets

APPARATUS AND TEST PROCEDURE FOR MEASURING THE COHESIVE, ADHESIVE, AND FRICTIONAL PROPERTIES OF BULK GRANULAR SOLIDS

BACKGROUND OF THE INVENTION

The present invention relates generally to bulk solids and more particularly to measuring cohesive, adhesive and frictional properties of bulk solids.

Measuring the cohesive, adhesive and frictional properties (sometimes called the Theological properties) of bulk solids has previously been accomplished by a split ring shear cell to which normal and shear forces are applied to a specimen of particulate solid confined between flat top and bottom disks and at the sides with top and bottom split rings that move with respect to each other. Examples of there testers include the Jenike tester and the Pechel tester. The magnitude of the normal and shear forces applied to the rings then determine the state of stress in the mass of particulates. Sometimes a tri-axial test cell is used in which a cylinder of bulk solids is subjected to a lateral pressure applied through a flexible membrane and an axial force from which the state of stress in determined. Most recently a uni-axial tester is used in which solids are consolidated uni-axially in a cylinder and then sheared along a conical surface that is coaxial with the cylinder.

Each of these testers and test methods share similar deficiencies. Each imposes a severely non-uniform stress and strain in the sample during the load application and each is difficult to interpret. For example, the Jenike type split ring shear cell develops a high stress concentration at the front of the ring being pushed by the shear load and at the back of the ring which remains stationary. This concentration is so severe that with cohesive bulk solids, a void often forms at both the front of the bottom ring and the back of the top ring of the test apparatus. This makes a proper analysis of the test results difficult at best and decreases both accuracy and precision of the test results. The split rotational ring tester causes a strain rate gradient from zero at the center to a maximum on the outer edge of the rings thus causing an ill-defined strain and stress state. The Tri-axial tester allows an uncontrolled shear plane to develop during sample failure. The uni-axial tester provides relatively uniform initial compaction. However, during failure a very non-uniform stress occurs at both the top and the bottom of the specimen.

All but the uni-axial tester are very difficult to interpret making them time consuming to run. For example, to measure the strength of a bulk solid at a single consolidation pressure with a split ring shear tester requires three to six tests to obtain enough data for proper interpretation. The tri-axial tester requires at least three cumbersome tests for a single strength value. While the uni-axial tester can produce one approximate strength value with a single test, an auxiliary test is required to obtain the internal frictional properties of the bulk solid.

There is thus a need in the art for a test apparatus and method for properties of bulk solids that provides uniform stress and strain in the sample during the load application and is uncomplicated to interpret.

SUMMARY OF THE INVENTION

The present invention advantageously addresses the needs above as well as other needs by providing a test apparatus and method for measuring cohesive, adhesive and frictional properties of bulk solids.

In one embodiment, the invention can be characterized as an apparatus for measuring properties of granular solids comprising an upper plate and a lower plate parallel to the upper plate. The upper plate is rotatably attached to a load application bracket such that the lower and upper plate may rotate around the bracket on an axis substantially parallel to a planar surface of the upper plate.

In another embodiment, the invention can be characterized as a method of testing bulk solids to determine an unconfined yield strength fc, an angle of internal friction phi and an effective angle of internal friction delta at a major principal consolidation pressure sigma1. A bulk solid is placed in a test apparatus as described above. Then, a known consolidation force CF is applied to the upper plate while the direction of applied force CF is substantially perpendicular to a planar surface of the upper plate. The test apparatus is rotated with respect to the direction of the applied force until a steady state movement of the bulk solid occurs between the parallel upper and lower plates of the apparatus. An angle of rotation alpha1 between the force direction and an axis perpendicular to a planar surface of the upper plate of the apparatus necessary to just maintain steady state movement is recorded. The angle alpha1 is reduced slightly to stop the steady state movement and maintain the force CF for a desired time of consolidation. The applied force CF is then reduced to near zero. The angle alpha1 is then increased to a failure angle and the applied force CF is increased to a condition of failure of the specimen at which point the value of the applied force CF at the condition of failure of the specimen is recorded as the failure force FF.

Finally, phi, fc, delta and sigma1 are calculated as follows:

phi=Arc tan((*CF* Sin(alpha1)–*FF* Sin(alpha2))/(*CF* Cos(alpha 1)–*FF* Cos(alpha2)))

*fc*=2(*FF/A*)((Sin(alpha2)Cos(phi)–Cos(alpha2)Sin(phi))/(1–Sin(phi))

delta=Arc sin(Sin(alpha1)/Cos(alpha1–phi))

sigma1=(*CF/A*)Sin(alpha1)(1+Sin(delta))/Sin(delta))

A better understanding of the features and advantages of the present invention will be obtained by reference to the following detailed description of the invention and accompanying drawings which set forth an illustrative embodiment in which the principles of the invention are utilized.

BRIEF DESCRIPTION OF THE DRAWINGS

The above and other aspects, features and advantages of the present invention will be more apparent from the following more particular description thereof, presented in conjunction with the following drawings wherein:

FIG. 2 is a side elevation view of the test apparatus of FIG. 1 except a lower half of the bulk solid is replaced by a solid plate of material representing a surface that the bulk solid may be required to slide on;

Corresponding reference characters indicate corresponding components throughout the several views of the drawings.

DETAILED DESCRIPTION OF THE PREFERRED EMBODIMENTS

The following description of the presently contemplated best mode of practicing the invention is not to be taken in a limiting sense, but is made merely for the purpose of describing the general principles of the invention. The scope of the invention should be determined with reference to the claims.

Figure 1:
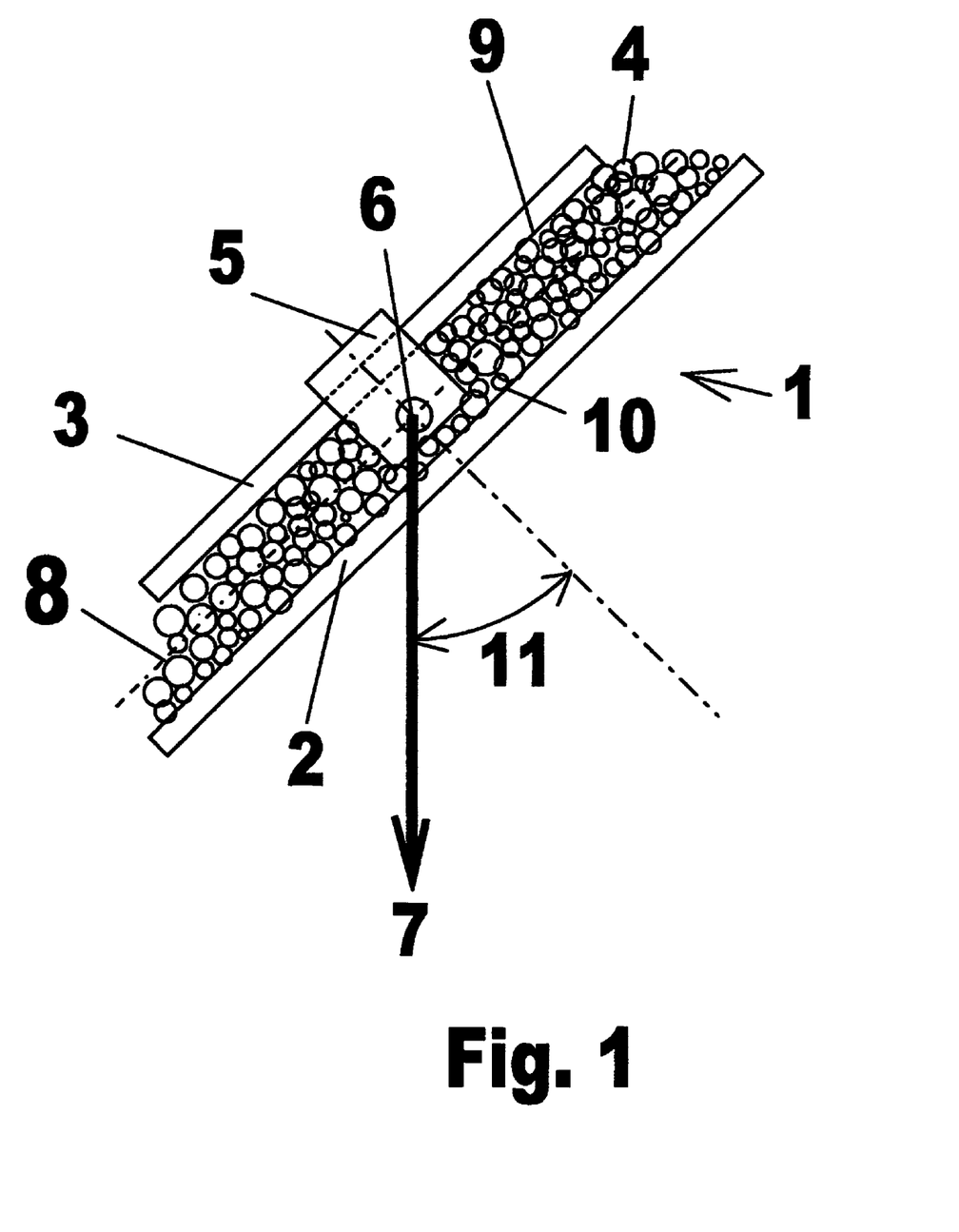
FIG. 1 is a side elevation view of a test apparatus in a tilted test position according to the present invention.

Referring to FIG. 1, shown is a side elevation view of a test apparatus 1 in a tilted test position according to the present invention.

FIG. 1 shows the basic test unit 1 comprised of a lower plate 2, an upper plate 3, and a load application bracket 5 securely attached to the upper plate 3 with a pin connection 6 to the applied force 7.

The entire assembly 1 rotates to an angle 11 with respect to an axis perpendicular to the plates and the direction applied force 7. The pin connection 6 allows this rotation with minimal frictional resistance and is located approximately at the center of the bulk solid specimen 4 between the plates 2 and 3. When the applied force is small with respect to the sum of the weight of plate 3, load bracket 5 and the material above the shear plane 8, it is essential that the force 7 directions be essentially in the same direction as gravity. The total force 7 acting on the shear plane 8 is then the applied force plus the sum of the weights of plate 2, bracket 5 and material 4 above the shear plane 8. If the applied force were not in the direction of gravity, the angle used in the analysis would need to be adjusted to the angle between the axis perpendicular to the plates 2 and 3 and the resulting total force acting on the test specimen. The surface of plates 2 and 3 in contact with the test material 4 must be rough enough to insure that the shear plane remain in the material 4 and not at the surfaces 9 or 10. This roughness can be achieved by cutting groves in the surfaces 9 and 10 of plates 2 and 3, by protruding pins from the surfaces 9 and 10 or by coating the surfaces with a rough media such as course sand paper.

Figure 2:
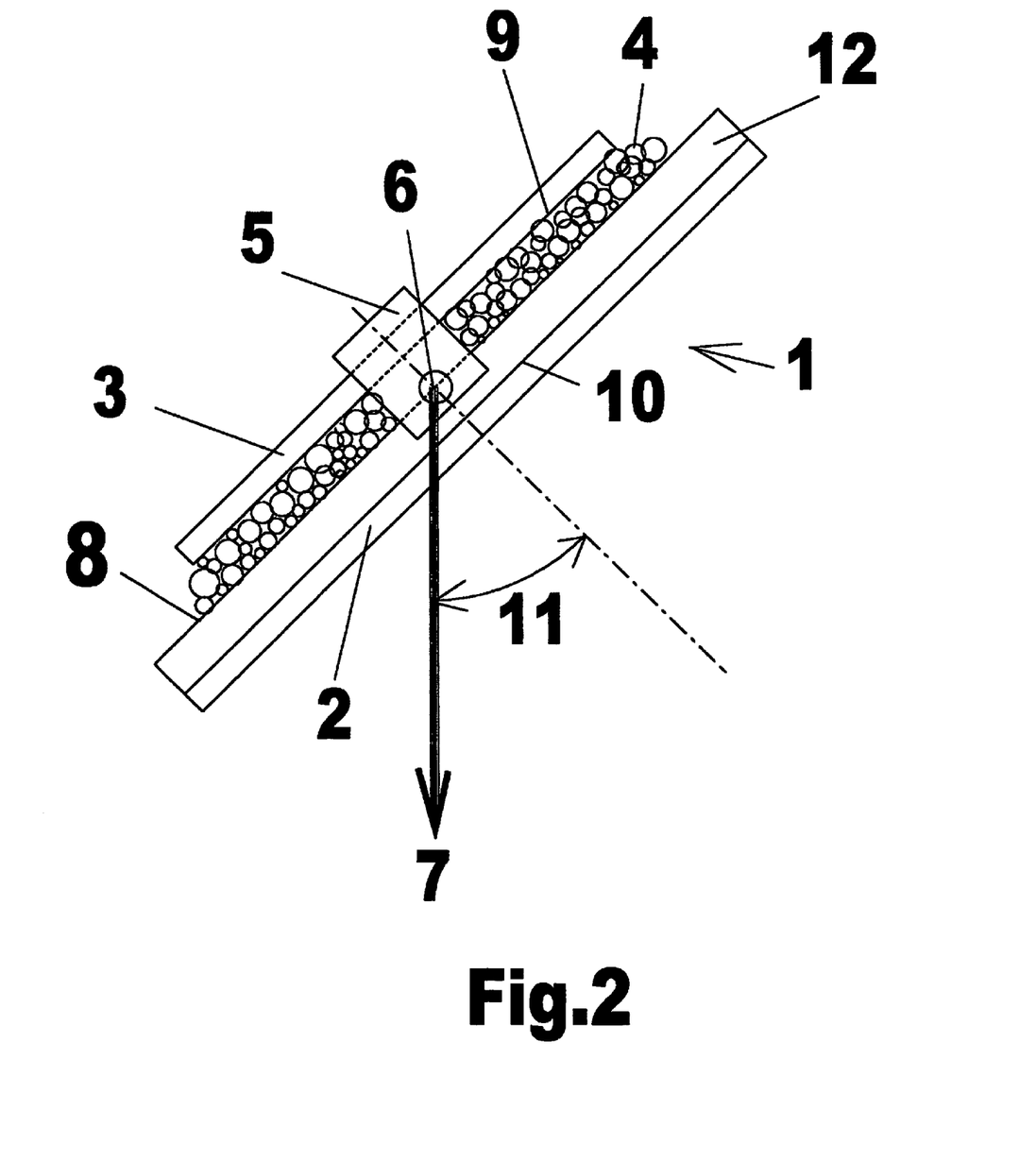

Referring next to FIG. 2, shown is a side elevation view of the test apparatus 1 of FIG. 1 except a lower half of the bulk solid 4 is replaced by a solid plate of material 12 representing a surface that the bulk solid may be required to slide on.

The shear plane 8 now corresponds with the surface of the plate 12. The roughness of surface 9 is still essential to prevent slippage on surface 9.

Figure 3:
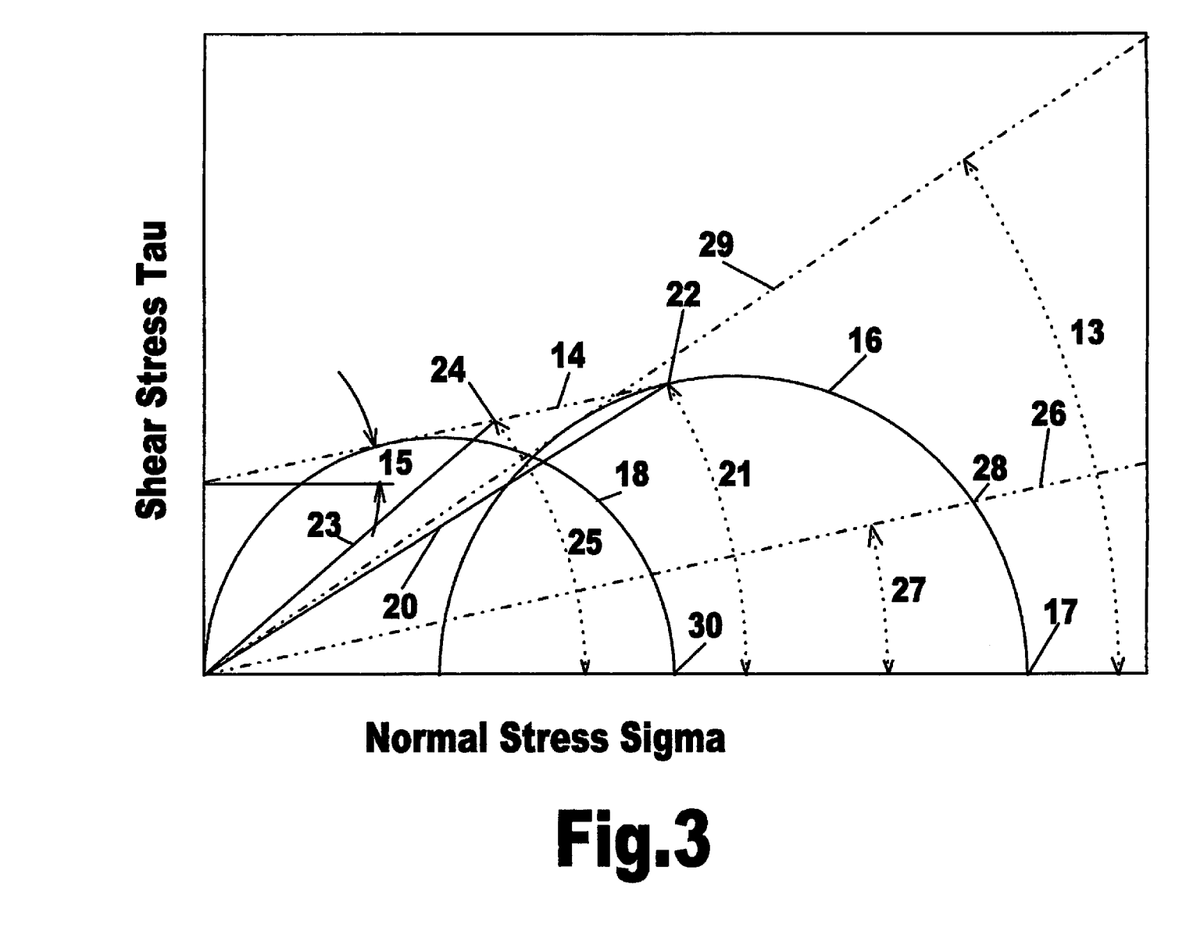
FIG. 3 is a graph of normal stress and shear stress acting on a shear plane between parallel plates of the test apparatus of FIG. 1 and the relation between these stresses during various stages of the test procedure according to the present invention.

Referring next to FIG. 3, shown is a graph of normal stress and shear stress acting on a shear plane between parallel plates of the test apparatus 1 of FIG. 1 and the relation between these stresses during various stages of the test procedure according to the present invention.

FIG. 3 shows the relation between shear stress tau and normal stress sigma in the test specimen during the test. The Mohr stress circles such as 16 and 18 in the figure represent the stresses. Two stress states are presented in the diagram. The first is given by the effective yield locus line 29 passing through the axes of the diagram (0,O) at the effective friction angle 13 (delta). The circle 16 is tangential to the effective yield locus 29. This circle represents a steady state deformation of a bulk solid at essentially a constant density. Such a state is approximated during flow of a bulk solid in a bin or feeder. The second stress state is given by circles tangent to the yield locus line 14. In general, this yield locus, characterized by the angle of internal friction angle 15 (phi), does not pass through the axes of the diagram (0,O) unless the bulk solid is cohesionless (has no strength). Both circles 18 and 16 are tangent to the yield locus 14 because both are conditions of yield. For circle 16 the condition is continuous yield and consequently this circle is also tangent to the effective yield Locus 29. For circle 18 the yield occurs suddenly as the strength is broken. Circle 18 passes through the axes (0,O) and consequently represents the unconfined yield stress condition of the bulk solid that has been consolidated by the steady state stress represented by circle 16. This strength is characterized by the unconfined yield strength fc given by the normal stress point 30. The consolidation causing fc is characterized by the major principal consolidation stress sigma1, the normal stress point 17. The object of the test using the apparatus in FIG. 1 is to determine phi, fc, delta and sigma1. The test procedure to determine phi, fc, delta and sigma1 is as follows:

1. With the angle 11 at zero, apply a known consolidation force CF (7).
2. Rotate the test apparatus with respect to the direction of the applied force until steady state flow of the bulk solid occurs between the parallel plates 2 and 3 of the apparatus.
3. Record the angle of rotation angle 11 between the force direction and the perpendicular to the plates of the apparatus necessary to just maintain the steady state movement as alpha1.
4. Reduce the angle 11 slightly to stop flow and maintain the force 7 for a desired time of consolidation.
5. Reduce the force 7 and angle 11 to near zero and then increase the angle 11 and force 7 to a failure conditions angle alpha2 and failure force FF. In general there are unlimited alpha, FF combinations that will cause failure. The results will be more accurate if alpha and FF are substantially different from steady state conditions. Alpha2 will generally be greater than the angle delta (13) unless the bulk solid is cohesionless and FF will be much less than CF unless the bulk solid is extremely cohesive.
6. The data collected can now be used in FIG. 3 to determine phi, fc, delta and sigma1 as follows:

1. Determine the length of line 20 as CF/A where A is the cross-sectional area of the test apparatus plate 3.
2. Determine the location of point 22 by setting angle 21 to the recorded steady state angle alpha1.

3. Determine the length of line 23 as FF/A where A is the cross-sectional area of the test apparatus plate 3.
4. Determine the location of point 24 by setting angle 25 to the recorded failure angle alpha2.
5. Draw line 14 between points 24 and 22 and measure the angle of internal fiction phi as angle 15.
6. Draw circle 18 tangent to line 24 and through point (0,O) and determine fc as point 30.
7. Draw circle 16 tangential to line 14 at point 22 and determine the Effective Yield Locus line 29 and delta angle 13.
8. Determine sigma1 at point 17. The above procedure can be expressed mathematically as follows:

$$phi = \text{Arc tan}((CF\,\text{Sin}(alpha1) - FF\,\text{Sin}(alpha2))/(CF\,\text{Cos}(alpha1) - FF\,\text{Cos}(alpha2)))$$

$$fc = 2(FF/A)(\text{Sin}(alpha2)\text{Cos}(phi) - \text{Cos}(alpha2)\text{Sin}(phi))/(1 - \text{Sin}(phi))$$

$$delta = \text{Arc sin}(\text{Sin}(alpha1)/\text{Cos}(alpha1 - phi))$$

$$sigma1 = (CF/A)\text{Sin}(alpha1)(1 + \text{Sin}(delta))/(\text{Cos}(phi)\,\text{Sin}(delta))$$

In some cases it may not be desirable to compact the bulk solid using a shearing action since this will not duplicate the desired stress conditions. Examples of this are when the strength required is that of a bulk solid inside of a bin without flow at the walls where the strength must represent the non-flowing material or the strength at a hopper outlet when a bin in initially loaded without flow or when the strength of a tablet that was compressed uni-axial is needed. The procedure in this case is to compact the sample with the angle 11 near zero at a load CFU equivalent to the desired major principal pressure sigma1=CFU/A for the required length of time consolidation. The load is reduced to near zero and the angle 11 increased as above to a failure angle alpha1 and force FF1. The test is repeated with the same consolidation load, time, and a different failure angle 11 (alpha2) greater than alpha1 and a new failure load FF2 less than FF1 is then determined. In general there is an unlimited number of alpha, FF combinations that will cause failure. The test accuracy is increased when the two selected are substantially different soon each other with FF less than CFU. The calculation is performed the same as above producing phi and fc as follows:

$$phi = \text{Arc tan}((FF1\,\text{Sin}(alpha1) - FF2\,\text{Sin}(alpha2))/(FF1\,\text{Cos}(alpha1) - FF1\,\text{Cos}(alpha2)))$$

$$fc = 2(FF/A)(\text{Sin}(alpha2)\text{Cos}(phi) - \text{Cos}(alpha2)\text{Sin}(phi)/(1 - \text{Sin}(phi)$$

The test procedure to determine the adhesive and the kinematic friction angle or angle of slide between the bulk solid 4 and the plate 12 in FIG. 2 is simply to apply force 7 (CFA) with angle 11 near zero. CFA/A represents the impact pressure sigma_i of material on the plate. The value of force 7 is then reduced to friction failure force FFF and the angle 11 is increased until failure occurs. This angle alpha_a is the adhesion angle for a bulk solid consolidated under impact pressure sigma_i with pressure FFF/A. The angle 11 is then reduced to that value just required to keep the bulk solid moving on the plate at a constant steady rate. The angle 11 (alpha_f) thus determined is the kinematic (moving) angle of slide or surface friction angle of the bulk solid on the plate tested.

Figure 4:
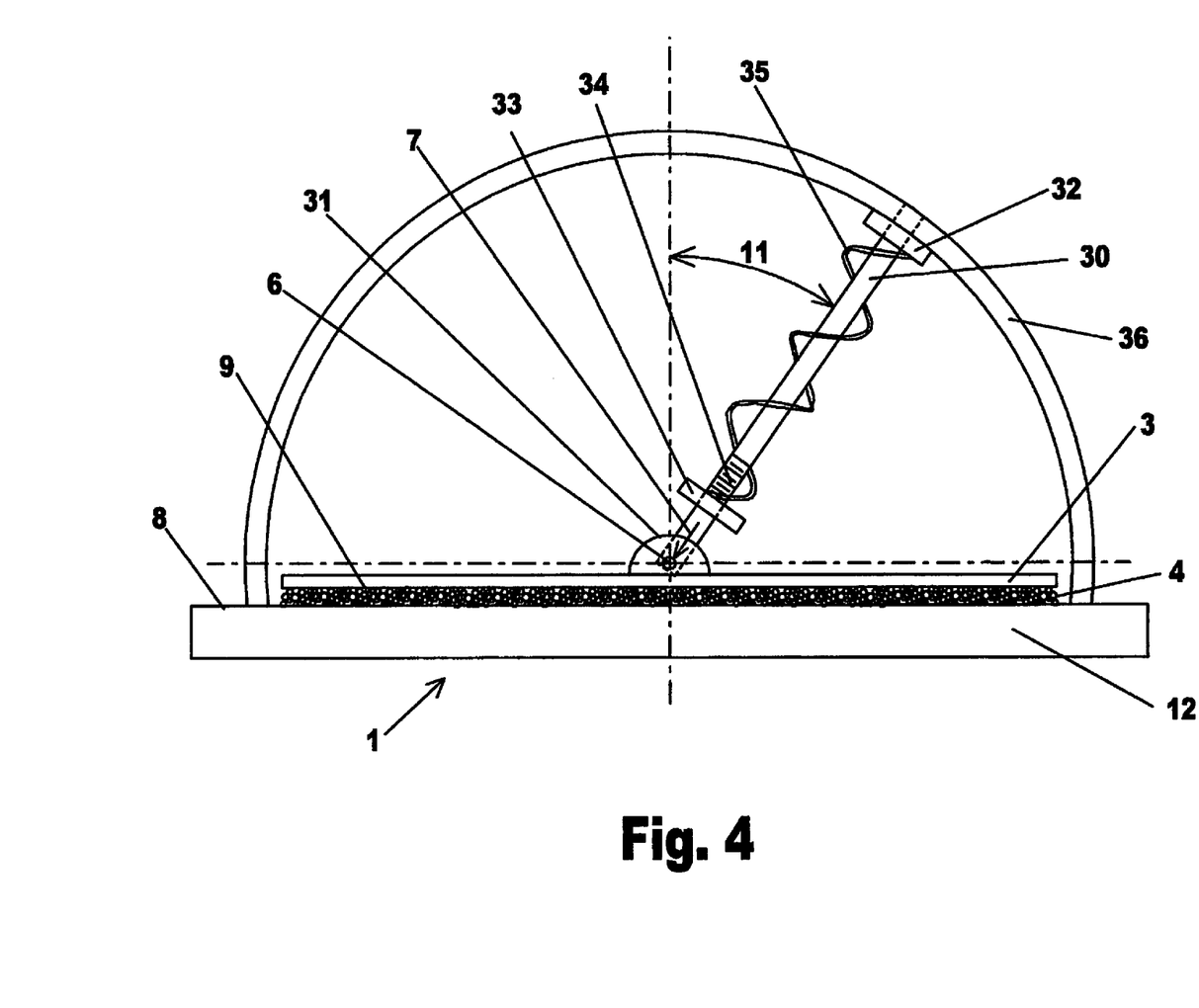
FIG. 4 is a side elevation view of the test apparatus of FIG. 1 showing a means of applying force to the test apparatus of FIG. 1 using a spring mounted in a circular guide according to the present invention.

Referring next to FIG. 4, shown is a side elevation view of the test apparatus 1 of FIG. 1 showing a means of applying force to the test apparatus of FIG. 1 using a spring 35 mounted in a circular guide 32 according to the present invention.

FIG. 4 shows a version of the apparatus 1 in which the force 7 is applied to the top of the plate 3 by means of a spring 35 that acts between the adjustable nut 33 and the non-attached washer and guide 32. The shaft 30 runs through the spring 35 and acts to stabilize the compressed spring. The circular guide 36 with its circle centered at the shaft 30 pivot point 6 allows for the adjustment of the angle 11 without changing the spring length and consequently the magnitude of force 7. Bracket 31 is attached securely to the top plate 3 so as to provide the pivot point 6 as close to the shear plane 8 as possible and thus minimize any misdistribution of the force 7 onto the material 4. The force 7 is adjusted in magnitude by advancing the nut 33 on the threads 34 of the shaft 30.

Figure 5:
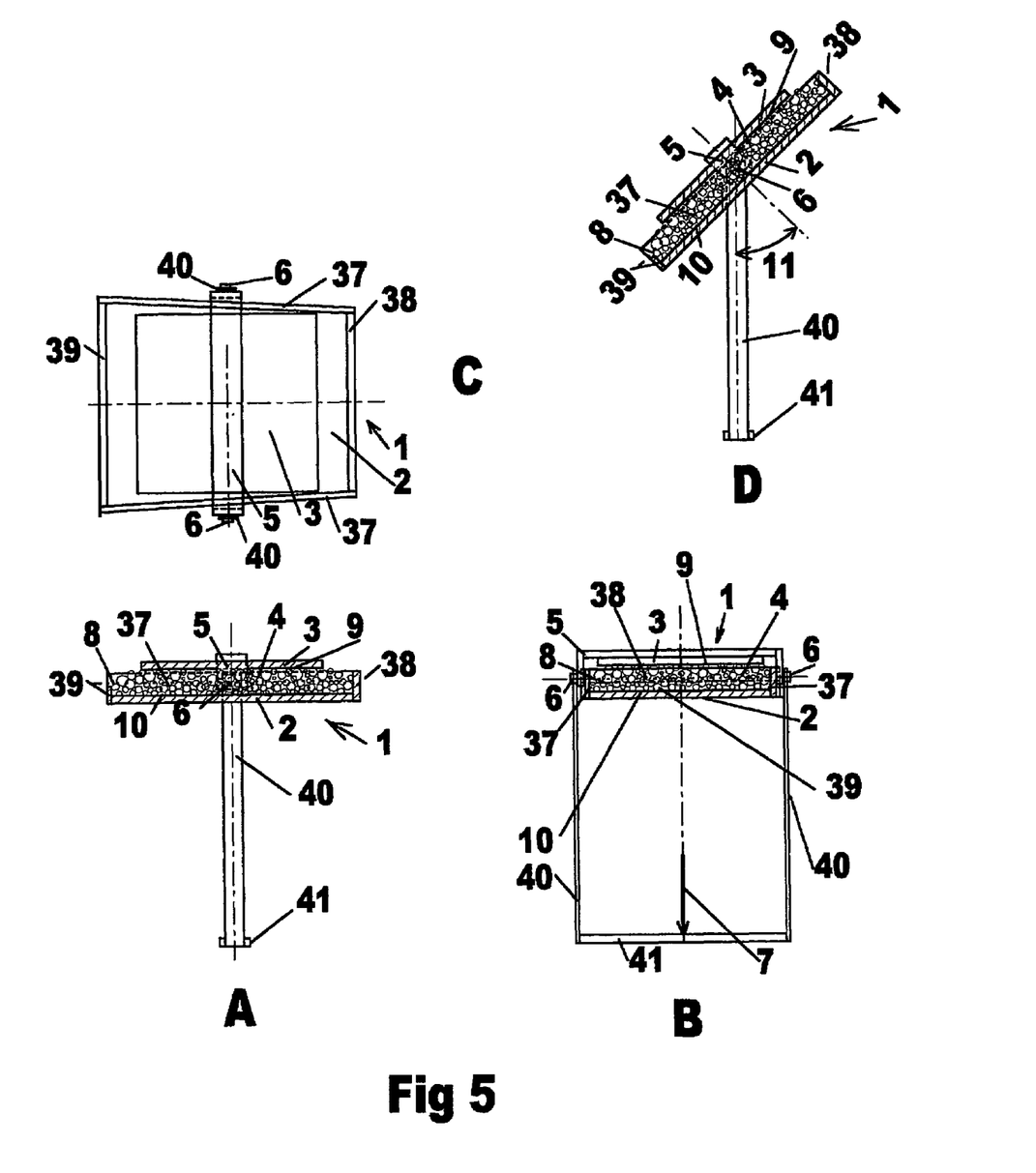
FIGS. 5A through 5C are side elevation, front elevation and top planar views, respectively, of the test apparatus of FIG. 1 showing alternate means of applying force according to the present invention.
FIG. 5D is a side elevation view of the test apparatus of FIGS. 5A-5C in a tilted position.

Referring next to FIGS. 5A through 5C, shown are side elevation, front elevation and top planar views, respectively, of the test apparatus of FIG. 1 showing alternate means of applying force according to the present invention. Also, FIG. 5D is a side elevation view of the test apparatus of FIGS. 5A-5C in a tilted position This embodiment is used when the bulk solid has little cohesion and might otherwise spill from the edges of the apparatus 1. The sides 37 are secured to the bottom plate 2 with an increasing distance between them in the direction of movement of top 2 so that end plate 38 is shorter than end plate 39. The difference in length of plate 38 and 39 need only provide a frictional force relief for material 4 moving with respect to the side plates 37.

It is essential that end plate 39 not protrude up to the shear plane 8 and thus causes a pressure concentration on the sample. The force 7 is applied to the center of the upper plate 3 by means of a yoke composed of pivoting side supports 40 and connecting cross support 41. As with other versions of the apparatus, surfaces 9 and 10 must be rough.

Figure 6:
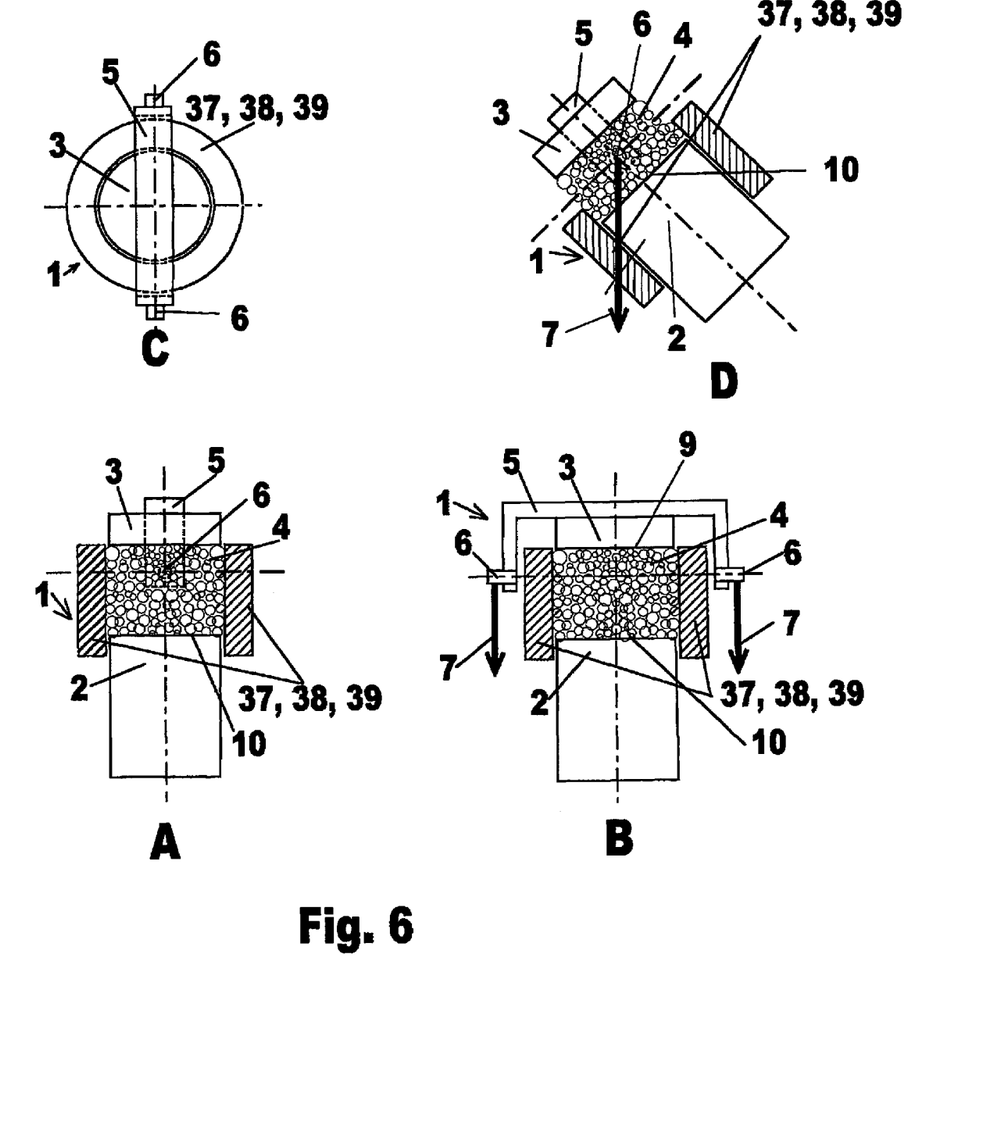
FIGS. 6A through 6C are side elevation, front elevation and top planar views, respectively, of a test apparatus according to the present invention for use with bulk solids having a large cohesive strength.
FIG. 6D is a side elevation view of the test apparatus of FIGS. 6A-6C in a tilted position and ready for the failure part of the test.

Referring next to FIGS. 6A through 6C, shown are side elevation, front elevation and top planar views, respectively, of a test apparatus according to the present invention for use with bulk solids having a large cohesive strength. Also, FIG. 6D is a side elevation view of the test apparatus of FIGS. 6A-6C in a tilted position and ready for the failure part of the test.

In this case, a solid hollow cylinder 37,38,39 that totally enshrouds the material 4 during compaction acts as the side and end containment plates 37,38 and 39. The lower plate 2 fits inside of the shroud to allow slippage during compaction and thus create a more uniform compaction of the sample as it compresses significantly during the uni-axial compaction stage of testing. FIG. 6D shows the test apparatus in a tilted position ready for the failure mode of testing with the shroud 37,38,39 pushed down to expose the shear plane 8. The test and analysis is preformed in the same way as with the uni-axial compression test described earlier.

Figure 7:
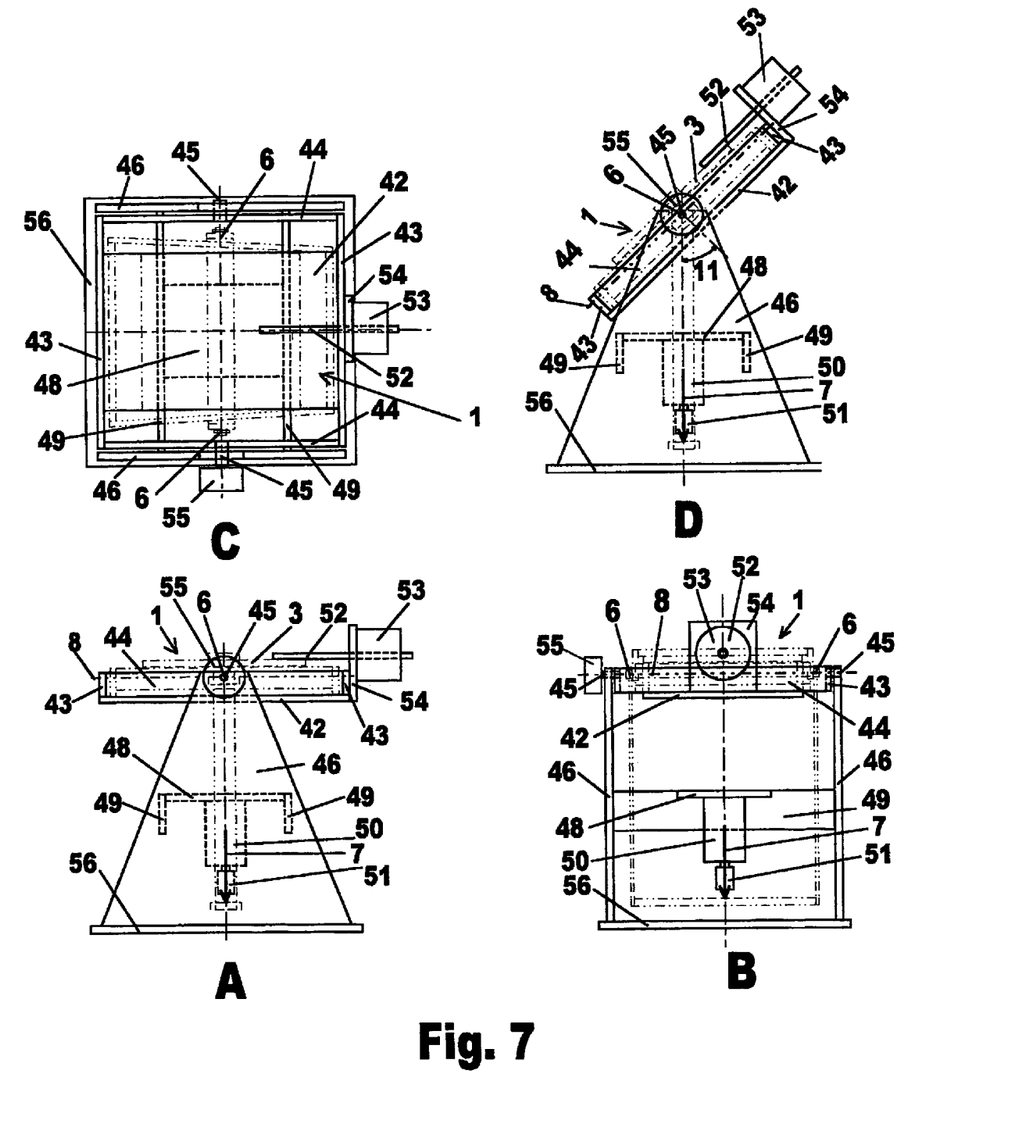
FIGS. 7A through 7C are side elevation, front elevation and top planar views, respectively, of the test apparatus of FIG. 1 incorporating a test stand capable of applying force, rotating the test apparatus and monitoring the motion of the test apparatus during testing according to the present invention.
FIG. 7D is a side elevation view of the test apparatus of FIGS. 7A-7C in a tilted position.

Referring next to FIGS. 7A through 7C, shown are side elevation, front elevation and top planar views, respectively, of the test apparatus of FIG. 1 incorporating a test stand capable of applying force, rotating the test apparatus and monitoring the motion of the test apparatus during testing according to the present invention. Also, FIG. 7D is a side elevation view of the test apparatus of FIGS. 7A-7C in a tilted position.

The apparatus 1 sits on a tilting support plate 42 that is hung from cross-supports 43. Supports 43 are secured to the end support plates 44 which are in turn supported by the pivot pins 45. The pivot pins 45 are secured to the major support end plates 46 which are secured to the base plate 56. A plate 48 holds in position a linear actuator 50 and is supported by cross plates 49 which tie securely to the major support plates 46.

The linear actuator 50 pushes the load cell 51 onto the load yoke cross-support 56 to provide force 7. The load cell 51 is zeroed to account for the weight of the load yoke supports 40, the top plate 3 and the weight of the material 4 (shown in FIG. 1) above the shear plane 8 so that the measured force 7 is the total applied force at the shear plane 8. The purpose of this many faceted support system is to allow the vertical yoke supports 40 to penetrate the support system without interference even when the support plate 42 is tilted.

A rod 52 is attached securely to the apparatus top plate 3 so as to move whenever the top plate moves. The rod attaches to the core of the linear variable differential transformer (LVDT) 53 to provide a position of the apparatus top plate 3. The LVDT 53 is secured to the tilting cross plate 43 by the bracket 54. A rotational drive 55 provides the necessary control of the rotational motion. The rotational drive is preferably a stepper motor with a counter to sense the angle 11, but may also be, for example, a hand crank with a protractor to indicate the angle. The actuated load cell could optionally be a stack of weights and the LVDT 53 could also optionally be eliminated and the motion of plate 3 simply observed visually. An actuated load cell that senses the pull on rod 52 and adjusts the allowable position accordingly could optionally be used instead of the LVDT 53.

Figure 8:
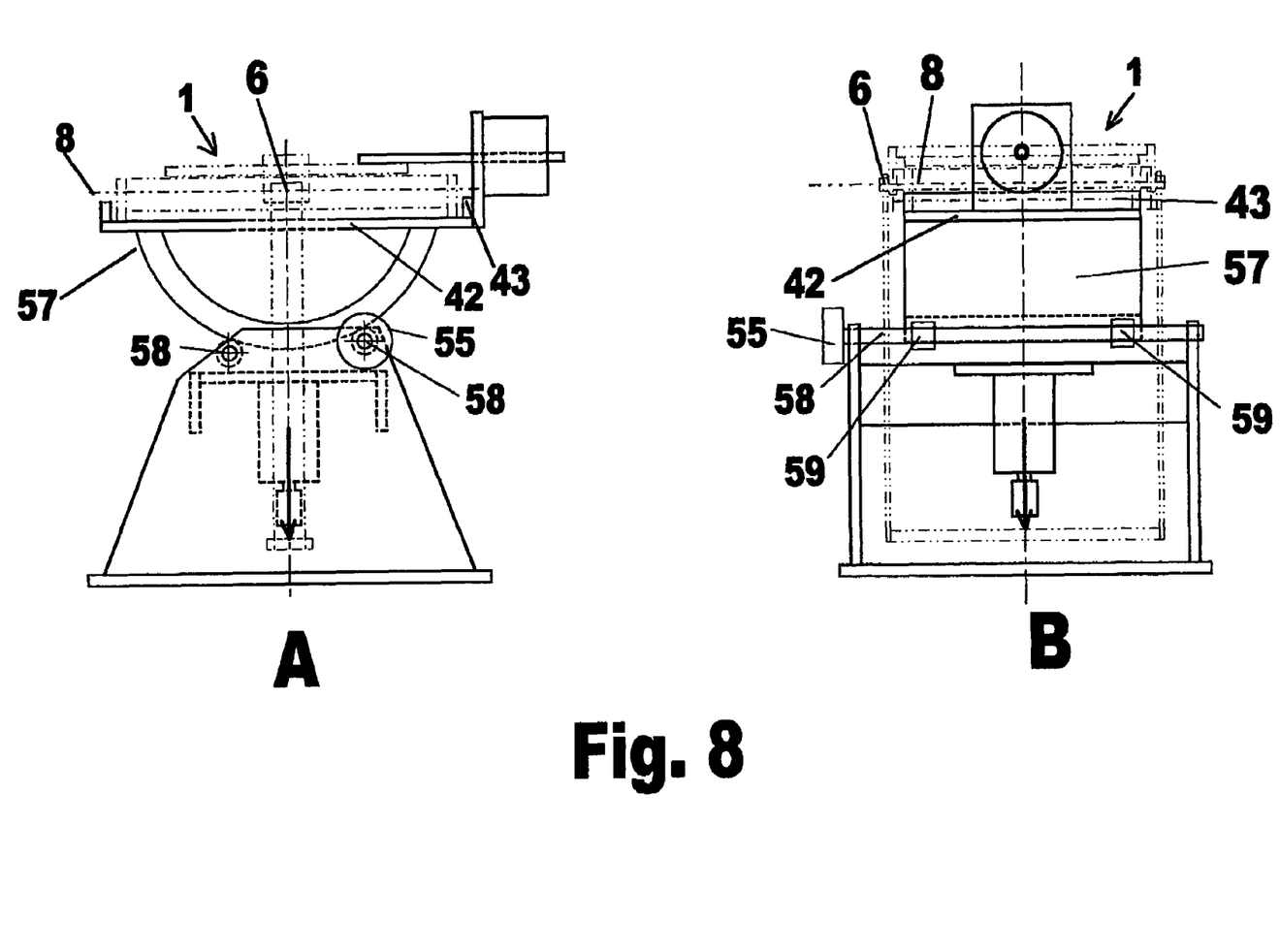
FIGS. 8A and 8B are side and front elevation views, respectively, of the test apparatus of FIG. 1 incorporating alternate means of support and rotation according to the present invention.

Referring next to FIGS. 8A and 8B, shown are side and front elevation views, respectively, of the test apparatus of FIG. 1 incorporating alternate means of support and rotation according to the present invention.

A portion of a cylinder 57 is attached to plate 42 such that when the test unit is rotated on supports 59, which are mounted on shafts 58, the rotation occurs essentially about the center of the shear plane 8 at the rotation axes 6 of the load hanger. The motion of rotation is provided by the actuator 55 which turns the shaft 58 that is attached to the supports 59.

While the invention herein disclosed has been described by means of specific embodiments and applications thereof, numerous modifications and variations could be made thereto by those skilled in the art without departing from the scope of the invention set forth in the claims.

What is claimed is:

1. An apparatus for measuring properties of granular solids comprising:
   an upper plate; and
   a lower plate parallel to the upper plate, and the upper plate rotatably attached to a load application bracket such that the upper plate may rotate about an axis substantially parallel to a planar surface of the upper plate, wherein the upper and lower plates are separated by a specimen of bulk solid.

2. The apparatus of claim 1, wherein the upper and lower plates are unrestricted with respect to each other such that relative movement between the plates is allowed and the plates are allowed to follow movement of the bulk solid and shear the bulk solid in response to an applied load.

3. The apparatus of claim 2 wherein a lower plate surface in contact with the bulk solid is roughened.

4. The apparatus of claim 2 wherein upper and lower plate surfaces in contact with the bulk solid are roughened.

5. The apparatus of claim 2 further comprising:
   a weight hingedly attached to the load application bracket via arms extending from the bracket on each side of the upper plate and past the lower plate; and
   a support table on which the lower plate rests on an upper surface of the table that pivots.

6. A test apparatus of claim 2 further comprising:
   a spring mechanism; and
   a circular guide, the spring mechanism located between the upper plate and the circular guide, the spring mechanism slidably attached to the circular guide and operable for applying force to the upper plate.

7. A method of testing bulk solids to determine an unconfined yield strength fc, an angle of internal friction phi and an effective angle of internal friction delta at a major principal consolidation pressure sigma 1 comprising the steps of:
   placing bulk solid in a test apparatus comprising an upper plate, a lower plate parallel to the upper plate and the upper plate rotatably attached to a load application bracket such that the lower and upper plate may rotate about an axis substantially parallel to a planar surface of the upper plate;
   applying a known consolidation force CF to the upper plate while the direction of applied force CF is substantially perpendicular to a planar surface of the upper plate;
   rotating the test apparatus with respect to the direction of the applied force until a steady state movement of the bulk solid occurs between the parallel upper and lower plates of the apparatus;
   recording an angle of rotation alpha 1 between the
   force direction and an axis perpendicular to a planar surface of the upper plate of the apparatus necessary to just maintain steady state movement;
   reducing the angle alpha 1 slightly to stop the steady state movement and maintain the force CF for a desired time of consolidation;
   reducing the applied force CF to near zero;
   increasing the angle alpha 1 to a failure angle;
   increasing the applied force CF to a condition of failure of the specimen; and
   recording the applied force CF at the condition of failure of the specimen value as the failure force FF; and
   calculating phi, fc, delta and sigma 1 as follows:

phi=Arc tan((CF Sin(alpha1)−FF Sin(alpha2))/(CF Cos(alpha1)−FF Cos(alpha2)))

fc=2(FF/A) Sin(alpha2)Cos(phi)−Cos(alpha2)Sin(phi)/(1−Sin(phi))

delta=Arc sin(Sin(alpha1)/Cos(alpha1−phi))

sigma1=(CF/A)Sin(alpha1)(1+Sin(delta))/(Cos(phi)Sin(delta)).

8. The method of claim 7, further comprising the step of measuring bulk solids flow properties as a function of a strain rate applied during the steady state movement.

9. The method of claim 7 further comprising the step of measuring bulk solids flow properties as a function of strain rate applied during the condition of failure of the specimen.

10. A method of testing bulk solids to determine an unconfined yield strength fc and an angle of internal friction phi after the bulks solids being consolidated under a uni-axial compressive stress sigma1 comprising the steps of:
   placing bulk solid in a test apparatus comprising an upper plate, a lower plate parallel to the upper plate and the upper plate rotatably attached to a load application bracket such that the lower and upper plate may rotate about an axis substantially parallel to a planar surface of the upper plate;
   applying a consolidation force CFU while the direction of force CFU is substantially perpendicular to a planar surface of the upper plate and such that CPU/A=sigma 1, where A is the area of the upper plate;
   maintaining CFU for a desired length of consolidation time;
   reducing CFU to near zero;
   increasing an angle between an axis perpendicular to the parallel plates of the test apparatus and the direction of the force CFU to an angle alpha 1 greater than an effective angle of internal friction delta;

increasing the force CFU to a failure condition of the specimen;

recording the value of force at the condition of failure as FF1;

placing a new sample in the test apparatus;

applying the consolidation force CFU while the direction of force CFU is substantially perpendicular to a planar surface of the upper plate and such that CPU/A=sigma 1;

maintaining CFU for the same length of consolidation time as used previously;

reducing the force CFU to near zero;

increasing an angle between the axis perpendicular to the parallel plates of the test apparatus and the direction of the force CFU to a new angle alpha2 greater than alpha1;

increasing the force CFU to a failure condition;

recording the value of force at the condition of failure as FF2; and calculating phi and fc as follows:

phi=Arc tan((FF1 Sin(alpha1)−FF2 Sin(alpha2))/(FF1 Cos(alpha1)−FF2 Cos(alpha2)))

fc=2(FF2/A)Sin(alpha2)/Cos(phi).

11. The method of claim 10 further comprising the step of measuring bulk solids flow properties as a function of strain rate applied during the condition of failure of the specimen.

12. A method of testing bulk solids to determine an adhesive and kinematic friction angle between a bulk solid and a plate of material on which the bulk solid may be required to slide comprising the steps of:

placing bulk solid in a test apparatus comprising an upper plate, a lower plate parallel to the upper plate wherein the lower plate surface in contact with the bulk solid is roughened and wherein the upper plate is rotatably attached to a load application bracket such that the lower and upper plate may rotate about an axis substantially parallel to a planar surface of the upper plate;

applying a force CFA in a direction substantially perpendicular to a planar surface of the upper plate to a magnitude such that CFA/A represents the impact pressure sigma_i of material at the upper plate, where A is the area of the upper plate;

reducing the magnitude of the applied force CFA to a desired value FFF;

increasing an angle between an axis perpendicular to the parallel plates of the test apparatus and the direction of the force CFU until failure occurs at which point the value of the angle is the adhesion angle for a bulk solid consolidated under impact pressure sigma_i with normal pressure FFF/A;

reducing the angle between an axis perpendicular to the parallel plates of the test apparatus and the direction of the force CFU to a value just required to keep the bulk solid moving on the lower plate at a constant steady rate, at which point this value is the kinematic friction angle of the bulk solid on the lower plate.

* * * * *

UNITED STATES PATENT AND TRADEMARK OFFICE
CERTIFICATE OF CORRECTION

PATENT NO. : 7,451,666 B2  Page 1 of 1
APPLICATION NO. : 11/332077
DATED : November 18, 2008
INVENTOR(S) : Jerry R. Johanson It is certified that error appears in the above-identified patent and that said Letters Patent is hereby corrected as shown below:

Claim 7, column 8, line 4, delete "sigma 1" and insert --sigma1--(no space and no bolding).
Claim 7, column 8, line 18, delete "alpha 1" and insert --alpha1--(no space and no bolding).
Claim 7, column 8, line 22, delete "alpha 1" and insert --alpha1--(no space and no bolding).
Claim 7, column 8, line 26, delete "alpha 1" and insert --alpha1--(no space and no bolding).
Claim 7, column 8, line 31, delete "sigma 1" and insert --sigma1--(no space and no bolding).
Claim 7, column 8, line 32, delete "(alpha1)" and insert --(alpha1)--(no bolding).
Claim 10, column 8, line 52, delete "sigma1" and insert --sigma1--(no bolding).
Claim 10, column 8, line 61, delete "sigma 1" and insert --sigma1--(no space and no bolding).
Claim 10, column 9, line 1, delete "alpha 1" and insert --alpha1--(no space and no bolding).
Claim 10, column 9, line 6, delete "FF1" and insert --FF1--(no bolding).
Claim 10, column 9, line 10, delete "sigma 1" and insert --sigma1--(no space and no bolding).
Claim 10, column 9, line 16, delete "alpha2" and "alpha1" and insert --alpha2-- and --alpha1--(no bolding).
Claim 10, column 9, line 19, delete "FF2" and insert --FF2--(no bolding).

Signed and Sealed this

Twenty-fourth Day of March, 2009

JOHN DOLL
*Acting Director of the United States Patent and Trademark Office*